United States Patent
Calaresu et al.

(10) Patent No.: US 9,012,696 B2
(45) Date of Patent: Apr. 21, 2015

(54) PROCESS FOR THE ALKYLATION OF AROMATIC HYDROCARBONS WITH OLEFINS

(75) Inventors: Paolo Calaresu, Sassari (IT); Alessandro Del Seppia, Porto Mantovano-Mantova (IT); Elena Bencini, Cerese di Virgilio (IT); Giovanni Antonio Fois, Virgilio Mantua (IT); Alessandro Casalini, Mantua (IT)

(73) Assignee: Versalis S.p.A, San Donato Milanese (MI) (IT)

( * ) Notice: Subject to any disclaimer, the term of this patent is extended or adjusted under 35 U.S.C. 154(b) by 0 days.

(21) Appl. No.: 14/127,421

(22) PCT Filed: Jun. 21, 2012

(86) PCT No.: PCT/EP2012/061947
§ 371 (c)(1),
(2), (4) Date: Jan. 16, 2014

(87) PCT Pub. No.: WO2012/175601
PCT Pub. Date: Dec. 27, 2012

(65) Prior Publication Data
US 2014/0142348 A1    May 22, 2014

(30) Foreign Application Priority Data
Jun. 23, 2011 (IT) .......................... MI2011A001144

(51) Int. Cl.
*C07C 37/08* (2006.01)
*C07C 2/66* (2006.01)
*C07C 29/143* (2006.01)
*C07C 45/53* (2006.01)

(52) U.S. Cl.
CPC . *C07C 2/66* (2013.01); *C07C 37/08* (2013.01); *C07C 2529/70* (2013.01); *C07C 29/143* (2013.01); *C07C 45/53* (2013.01)

(58) Field of Classification Search
None
See application file for complete search history.

(56) References Cited

U.S. PATENT DOCUMENTS

| | | | | |
|---|---|---|---|---|
| 5,026,940 A | * | 6/1991 | Fellmann et al. | 585/467 |
| 6,841,704 B2 | * | 1/2005 | Sakuth et al. | 568/798 |
| 8,404,914 B2 | * | 3/2013 | Senoo et al. | 568/798 |
| 8,575,413 B2 | * | 11/2013 | Lorenzoni et al. | 585/446 |
| 2005/0137437 A1 | * | 6/2005 | Soloveichik et al. | 585/467 |

FOREIGN PATENT DOCUMENTS

| | | |
|---|---|---|
| EP | 0776876 A1 | 6/1997 |
| EP | 2298718 A1 | 3/2011 |
| WO | 9103443 A1 | 3/1991 |
| WO | 0162692 A1 | 8/2001 |
| WO | WO 2009/150974 A1 * | 12/2009 ................ C07C 2/86 |

OTHER PUBLICATIONS

Jacob, Bindhu, "A Comparative Study of Medium and Large Pore Zeolites in Alkylation Reactions", Thesis submitted to Coachin University of Science and Technology for the partial fulfilment of the requirement for the degree of Doctor of Philosophy in Chemistry, Department of Applied Chemistry, Kocki—682 022, Kerala, Feb. 1998.

* cited by examiner

*Primary Examiner* — Brian J Davis
(74) *Attorney, Agent, or Firm* — Tarolli, Sundheim, Covell & Tummino LLP

(57) ABSTRACT

Process for the alkylation of aromatic hydrocarbons by means of olefins containing from 2 to 8 carbon atoms, which comprises feeding the hydrocarbon, olefin, and possibly water, to the head of a fixed-bed reactor, operating with a "trickle flow" regime, containing at least one layer of a catalyst comprising a medium-or large-pore zeolite.

17 Claims, No Drawings

PROCESS FOR THE ALKYLATION OF AROMATIC HYDROCARBONS WITH OLEFINS

The present invention relates to a process for the alkylation of aromatic hydrocarbons with $C_2$-$C_8$ olefins.

More specifically, the present invention relates to a process for the alkylation of aromatic hydrocarbons containing from 6 to 10 carbon atoms with $C_2$-$C_8$ olefins.

Even more specifically, the present invention relates to a process for the alkylation of benzene with propylene, to obtain cumene, or with ethylene, to obtain ethylbenzene.

As is known, alkylated aromatic hydrocarbons are known chemical products that are used as intermediate products in numerous organic syntheses. Cumene, or isopropylbenzene, for example, is an important precursor for the production of phenol, in turn useful as intermediate for producing caprolactam from which nylon-6 is produced. Ethylbenzene is the precursor of styrene, starting monomer for the synthesis of important thermoplastic materials such as polystyrene, ABS, SAN resins and other products.

Cumene and ethylbenzene can be produced by the alkylation of benzene with propylene or ethylene in the presence of zeolitic catalysts such as X zeolite, Y zeolite or ZSM-5 zeolite. These catalysts have substituted or are substituting traditional acid catalysts such as phosphoric acid or diatomaceous earth, for processes operating with fixed-bed reactors, or aluminium trichloride for processes operating with fluid-bed reactors. These traditional catalysts, in fact, have created problems of an environmental nature, for example relating to the disposal of the exhausted catalysts, and safety of the production plants subject to the risk of corrosion by acid materials.

In accordance with this, U.S. Pat. No. 3,251,897 describes the alkylation of aromatic compounds in liquid phase, catalyzed by X, Y zeolites or by mordenite. U.S. Pat. No. 4,292,458 describes the use of zeolites of the ZSM-5 type by the alkylation of benzene with propylene.

Zeolites are therefore generally active in the alkylation of aromatic compounds with olefins, but have different behaviours with respect to the selectivity. The alkylation reaction is in fact accompanied by consecutive reactions, such as poly-alkylation, and parallel reactions such as the oligomerization of olefins to give oligomers, which can in turn act as alkylating agents. In order to increase the selectivity to monoalkylated products, it is customary to operate in excess of aromatic hydrocarbon. The best results in terms of activity and selectivity in the alkylation of aromatic compounds with olefins, in particular C2-C4, preferably in liquid phase, are currently obtained using beta zeolite as catalyst, as described in EP 439632, EP 687500, EP 847802. Excellent results are also obtained using MCM-22 zeolite as alkylation catalyst.

The objective of the present invention is therefore to provide an alkylation process of aromatic hydrocarbons with olefins containing from 2 to 8 carbon atoms, for example ethylene or propylene, which provides improved performances with respect to the processes of the prior art, allowing a reduction in the formation of polyalkylated hydrocarbons and other by-products deriving from consecutive reactions, further improving the reaction yields.

The object of the present invention therefore relates to a process for the alkylation of aromatic hydrocarbons with olefins containing from 2 to 8 carbon atoms, which comprises feeding the hydrocarbon, olefin, and possibly water, to the head of a fixed-bed reactor, operating with "trickle flow" regime, containing at least one layer of a catalyst which comprises a zeolite selected from medium-pore zeolites and large-pore zeolites.

A preferred aspect of the present invention relates to a process in continuous for the alkylation of aromatic hydrocarbons with $C_2$-$C_8$ olefins, possibly in the presence of water, carried out in a fixed-bed alkylation reactor, which comprises:
1. mixing at least one aromatic hydrocarbon (A), an olefin containing from 2 to 8 carbon atoms (B), a recycled stream coming from a discharge section of the alkylation reactor, and possibly water,
2. feeding the final mixture obtained, pre-heated to the reaction temperature, to the head of a fixed-bed alkylation reactor, operating under "trickle flow" regime, containing at least one layer of a catalyst comprising a medium-pore or large-pore zeolite;
3. cooling the reaction mixture in a discharge section to obtain an organic phase, comprising the alkylated aromatic hydrocarbon and possibly an aqueous phase;
4. subdividing the organic phase into a recycled stream (C), sent to the head of the alkylation reactor for the mixing phase with the reagents, and a final stream, comprising the alkylated aromatic hydrocarbon.

An even more preferred aspect of the present invention relates to a process in continuous for the alkylation of aromatic hydrocarbons with $C_2$-$C_8$ olefins, possibly in the presence of water, carried out in a fixed-bed alkylation reactor, which comprises:
1. mixing at least one aromatic hydrocarbon (A), and the $C_2$-$C_8$ olefin (B), with molar ratios A/B higher than 1, preferably ranging from 1.5 to 5;
2. diluting the mixture coming from step (a) with a recycled stream coming from a discharge section of the alkylation reactor, and possibly water, so as to have a recycling weight ratio C/AB between the recycled stream (C) and the reagent mixture (AB) ranging from 1.5:1 to 10:1;
3. feeding the final mixture obtained, preheated to the reaction temperature, to the head of the fixed-bed alkylation reactor, operating under "trickle flow" regime, containing at least one layer of a catalyst containing a medium-pore or large-pore zeolite;
4. cooling the reaction mixture, directly downstream of the alkylation reactor, in a discharge section, to obtain an organic phase, comprising the alkylated aromatic hydrocarbon, and possibly an aqueous phase;
5. subdividing the organic phase into a recycled stream (C), sent to the head of the alkylation reactor for the mixing phase with the reagents, and a final stream, comprising the alkylated aromatic hydrocarbon.

The final stream thus obtained, as described further on, can be sent to subsequent process steps.

According to an aspect of the present invention, the olefin can also be used in a mixture with the corresponding alcohol, i.e. with an alcohol having the same number of carbon atoms as the olefin and which, by alkylation, provides the same alkyl substituent. In this case, the molar ratio between the olefin and corresponding alcohol is preferably greater than 10 and even more preferably ranges from 100 to 15. When a mixture of olefin and the corresponding alcohol is used, the molar ratio between aromatic hydrocarbon and mixture of olefin and the corresponding alcohol is higher than 1, preferably ranging from 1.5 to 5.

According to the present invention, the aromatic hydrocarbon preferably contains from 6 to 10 carbon atoms and is even more preferably selected from benzene, toluene and xylenes.

Any $C_2$-$C_8$ olefin can be used in the present invention, even if ethylene, propylene, butene, hexene and cyclohexene are preferred. Particularly preferred olefins are ethylene and propylene.

In particular, when the aromatic hydrocarbon is benzene and the olefin is ethylene or propylene, said reagents are fed to the alkylation reactor with weight ratios benzene/olefin preferably ranging from 75/25 to 90/10, according to what has been previously specified in relation to the molar ratios between the process reagents.

According to an aspect of the present invention, it is possible to operate under substantially anhydrous conditions: under these conditions up to 50 ppm of water can be present.

According to another embodiment of the process of the present invention, water is added to the reagents, in a quantity preferably not greater than 6% with respect to the total mixture fed to the reactor.

In particular, the process of the present invention is conveniently used for the alkylation of benzene with ethylene to give ethylbenzene and for the alkylation of benzene with propylene to give cumene.

The stream of aromatic hydrocarbon and the stream of $C_2$-$C_8$ olefin, and possibly the water added, can be premixed and then joined to the recycled stream (C), if said stream is used. Alternatively, the streams can be mixed together, each already at the reaction temperature or they can first be mixed together and then preheated to the operating temperature present inside the alkylation reactor.

If the recycled stream is used, the fresh reagents (AB) are mixed with said stream (C), with weight ratios C/AB preferably ranging from 2:1 to 6:1. The recycled stream, corresponding to part of the stream recovered from the reaction product after separation by demixing or decanting from the aqueous phase possibly present, is a stream mainly comprising the alkylated product and aromatic reagent in excess. In said recycled stream, if water has been added to the reagents that are subjected to alkylation, a concentration of water equal to its solubility under the conditions of temperature and pressure of recycling can be present.

The flow-rate of the reagents to the alkylation reactor is such as to provide a WHSV (Weight Hourly Space Velocity) which ranges from 1 to 8 hours$^{-1}$, for example and preferably from 2 to 6 hours$^{-1}$.

The alkylation reaction is carried out in continuous, and the reaction mixture, possibly also comprising the recycled stream, is fed to the head of the alkylation reactor operating with a "trickle flow" regime. "Trickle flow" regime comprises operating in a three-phase, gas-liquid-solid situation wherein the catalyst is the solid phase, enveloped by the liquid and by the gas that pass through it in equicurrent from the top downwards, and it is a fluid-dynamic operative condition of a reactor for liquid/vapour reactions well-known to experts in the field, and described in detail in literature, for example in AIChE Journal, 1991, vol. 37 (2), page 202; Ind. Eng. Chem. Res., 1990, Vol. 29 (5), page 738; Ind. Eng. Chem. Res. 1997, 36, 3292-3314.

The flow regime type "trickle flow" can be obtained by managing the operative conditions of the alkylation reactor so as to have a gaseous phase essentially consisting of the reagents, and a liquid phase essentially consisting of the alkylation product, i.e. the monoalkylated and polyalkylated aromatic hydrocarbon. The water possibly added to the reagents is distributed between the gaseous phase and the liquid phase, and is prevalently in gaseous phase.

Without adhering to any theory, it is held that under the conditions of the present invention, the liquid phase percolates through the catalytic bed and descends towards the bottom of the reactor causing only a partial wettability of the catalytic bed. This reduced contact with the catalytic bed could be the reason for which there is a lesser tendency of the alkylated hydrocarbon to produce polyalkylated hydrocarbons.

The vapour phase, on the contrary, essentially consisting of the reagents, completely impregnates the catalytic bed, maximizing the contact with the catalytic active sites.

The reaction temperature inside the alkylation reactor preferably ranges from 160 to 250° C., more preferably from 180 to 230° C., with an internal pressure ranging from 1 to 10 MPa, more preferably from 1 to 5 MPa. An expert in the field is capable, for each aromatic substrate and for each olefin, of selecting the temperature and pressure conditions that cause the presence of a gaseous phase and a liquid phase in the alkylation reactor, and in particular the pressure and temperature conditions that make it possible to operate with the reagents that are in gas phase and the products that are in liquid phase.

Any catalyst containing a medium-pore zeolite can be used in the process, object of the present invention. A MCM-22 zeolite is preferably used.

Any catalyst containing a large-pore zeolite can be used in the process, object of the present invention, wherein large-pore zeolite refers to a zeolite in which the pore openings consist of 12 tetrahedra. This corresponds in particular for zeolites based on silicon oxide and aluminium oxide, to pore openings consisting of twelve atoms, selected from silicon atoms and aluminium atoms, in tetrahedral coordination bound to each other by the sharing of an oxygen atom. Large-pore zeolites that can be conveniently used are zeolites of the type MTW, FAU, BEA, MAZ, MOR, OFF, SAPO-5, SAPO-11, and are preferably zeolites of the FAU, MTW and BEA type.

MCM-22 zeolite is described for example in Science, 264, 1910-1913 (1994) and in U.S. Pat. No. 4,954,325.

FAU-type zeolites, and in particular zeolite Y, are described for example in U.S. Pat. No. 3,130,007 and in "Verified Synthesis of Zeolitic materials" H. Robson Editor, Elsevier, second revised edition 2001.

Among zeolites of the MTW type, ZSM-12 zeolite is preferred. This is a porous crystalline material based on oxides which, in its anhydrous or calcined form, has a molar composition of the oxides corresponding to the following formula:

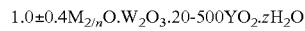

$$1.0 \pm 0.4 M_{2/n}O.W_2O_3.20\text{-}500YO_2.zH_2O$$

wherein M is H$^+$ and/or a cation of an alkaline or alkaline-earth metal having a valence n, W is selected from aluminium, gallium or mixtures thereof, Y is selected from silicon and germanium, z varies from 0 to 60. M is preferably selected from hydrogen, sodium, potassium or mixtures thereof. W is preferably aluminium and Y is preferably silicon. W can be at least partially substituted by boron, iron or mixtures thereof. More detailed information on ZSM-12 zeolite is available in U.S. Pat. No. 3,832,449, in Ernst et al., Zeolites, September 1987, Vol. 7 and in Toktarev & Ione, Chon et al., *Progress in Zeolite and Microporous Material*, SSSC, Vol. 105, 1997.

Zeolites of the BEA type and in particular beta zeolite, are described in U.S. Pat. No. 3,308,069. Beta zeolite is a porous crystalline material having the composition:

$$[(x/n)M(1 \pm 0.1-x)TEA]AlO_2.ySiO_2.wH_2O$$

wherein n is in the oxidation state of M, x is less than 1, y ranges from 5 to 100, w from 0 to 4, M is a metal selected from those of groups IA, IIA, IIIA of the Periodic System or from transition metals and TEA is tetraethylammonium hydroxide. Beta zeolite is also described for example in U.S. Pat. No. 4,642,226 and EP 159846.

According to an aspect of the present invention, the large-pore zeolite, is preferably used in the form in which the cationic sites present in its structure are occupied for at least 50% by hydrogen ions. In particular, it is preferable for at least 90% of the cationic sites to be occupied by hydrogen ions.

The catalyst containing the medium- or large-pore zeolite is positioned in the reactor as a fixed bed that can consist of a single layer or a plurality of layers. The layers can be separated from each other so that a heat exchanger can be positioned in the intermediate space, that helps keep a constant vertical temperature profile inside the reactor.

The catalyst containing the medium- or large-pore zeolite can be used as such or in bound form with an inorganic ligand. It can be in the form of extruded pellets or microspheres obtained by the technique known as spray-drying. These techniques are used with both the medium- or large-pore zeolite as such, or with the medium- or large-pore zeolite bound with an inorganic ligand. The inorganic ligand can be alumina, silica, silica-alumina, titania, zirconia or clay. Alumina is the preferred ligand. If adopted, the inorganic ligand is used in such quantities as to give zeolite/ligand weight ratios ranging from 5/95 to 95/5, preferably from 20/80 to 80/20.

Using the process of the present invention, a drastic reduction in the formation of polyalkylated products is obtained, with respect to the corresponding processes which do not use reaction conditions with a "trickle-flow" regime, wherein said conditions with a "trickle-flow" regime, well-known to the experts in the field, comprise:

positioning of the fixed bed catalyst,
characteristic fluid-dynamic conditions and/or thermodynamic conditions inside the reactor associated with the fact that the feeding of the reagents is effected at the head of the reactor, with the fact that a gas phase coexist preferably and essentially consisting of the reagents and a liquid phase preferably and essentially consisting of the reaction products, wherein both phases pass through the catalytic bed in equicurrent,
particular correlations between the linear rates of the liquid phase and gaseous phase.

Furthermore, recycling, when used, favours the disposal of heat, particularly inhibiting the formation of further by-products.

The reduction in polyalkylated products is important as it allows a reduction in the dimensions of the transalkylation section and distillation columns, downstream of the alkylation section, which represent a critical part of the overall alkylation process. This also leads to further advantages in terms of the consumption of transalkylation catalyst and utilities.

At the end of the alkylation step, the reaction mixture, comprising the alkylaromatic hydrocarbon, is discharged from the reactor and sent to a section where it is cooled to room temperature, for example from 20 to 40° C., and separated from the water possibly present. The separation from the water preferably takes place by demixing/decanting in specific equipment, where the organic phase is separated from the aqueous phase.

The organic stream that is collected after demixing can be divided into two sub-streams: one is used for recycling, whereas the non-recycled part can have a purity which is such that it does not require subsequent treatment, or it can be sent to the remaining sections of the overall alkylation process which essentially comprise the transalkylation section, where the polyalkylated aromatic hydrocarbons are substantially transformed into monoalkylated product, and the purification section, where the monoalkylated aromatic product is recovered with a purity degree higher than 95% by weight.

If the monoalkylated aromatic product is cumene, this can be used, as is known, for producing phenol and acetone. The acetone produced together with the phenol can be recovered and transformed into isopropanol, and then propylene, to be used as reagent in the alkylation process, object of the present invention.

A further object of the present invention therefore relates to a process for preparing phenol comprising the following steps:
(a) alkylation of benzene with propylene, to give cumene, realized in a fixed bed reactor containing at least one layer of a catalyst containing a medium- or large-pore zeolite, which comprises feeding benzene and propylene, to the head of the alkylation reactor and operating in "trickle flow" regime, said alkylation being effected in accordance with one or more of the operative aspects specified above,
(b) oxidation of the cumene thus obtained,
(c) treatment of cumyl hydroperoxide with acids in order to obtain a mixture of phenol and acetone,
(d) hydrogenation of acetone to isopropanol,
(e) dehydration of isopropanol to propylene which is recycled to step (a).

The invention claimed is:
1. A process for the alkylation of aromatic hydrocarbons by means of olefins containing from 2 to 8 carbon atoms comprising:
feeding the hydrocarbon, the olefin, and optionally water, to the head of a fixed-bed reactor, operating under "trickle flow" regime, containing at least one layer of a catalyst comprising a medium-pore zeolite or a large-pore zeolite.

2. The process according to claim 1, carried out continuously, which comprises:
(a) mixing, in liquid phase, at least one aromatic hydrocarbon (A), a $C_2$-$C_8$ olefin (B), a recycled stream (C) coming from a discharge section of the alkylation reactor, and optionally water;
(b) feeding the mixture obtained in step (a), pre-heated to the reaction temperature, to the head of the fixed-bed alkylation reactor, operating under "trickle flow" regime, containing at least one layer of a catalyst comprising a medium-pore or large-pore zeolite;
(c) cooling the reaction mixture in a discharge section to obtain an organic phase, comprising the alkylated aromatic hydrocarbon; and
(d) subdividing the organic phase into a recycled stream (C), sent to the head of the alkylation reactor for the mixing phase with the reagents, and a final stream, comprising the alkylated aromatic hydrocarbon.

3. The continuous process according to claim 1, which comprises:
(a) mixing, in liquid phase, at least one aromatic hydrocarbon (A), and the $C_2$-$C_8$ olefin (B), with molar ratios A/B higher than 1;
(b) diluting the mixture coming from step (a) with a recycled stream coming from a discharge section of the alkylation reactor, and optionally water, so as to have a recycling weight ratio C/AB between the recycled stream (C) and the reagent mixture (AB) ranging from 1.5:1 to 10:1;
(c) feeding the final mixture obtained, preheated to the reaction temperature, to the head of the fixed-bed alkylation reactor, operating under "trickle flow" regime, containing at least one layer of catalyst comprising a zeolite selected from medium-pore zeolites and large-pore zeolites;

(d) cooling the reaction mixture, directly downstream of the alkylation reactor, in a discharge section, to obtain an organic phase, comprising the alkylated aromatic hydrocarbon; and (e) subdividing the organic phase into a recycled stream (C), sent to the head of the alkylation reactor for the mixing phase with the reagents, and a final stream, comprising the alkylated aromatic hydrocarbon.

4. The process according to claim 1, wherein in the alkylation reactor, the aromatic hydrocarbon and olefin are in gas phase and the alkylation products are in liquid phase.

5. The process according to claim 3, wherein the recycling weight ratio C/AB between the recycled stream (C) and the reagent mixture (AB) ranges from 2:1 to 6:1.

6. The process according to claim 1, wherein the flow-rate of the reagents to the alkylation reactor is such as to provide a WHSV (Weight Hourly Space Velocity) ranging from 1 to 8 $hrs^{-1}$.

7. The process according to claim 1, wherein the reaction temperature inside the alkylation reactor ranges from 160 to 250° C. and the internal pressure ranges from 1 to 10 MPa.

8. The process according to claim 1, wherein the aromatic hydrocarbon is selected from benzene, toluene and xylene.

9. The process according to claim 1, wherein the olefin is selected from ethylene and propylene.

10. The process according to claim 1, wherein the zeolite is a large-pore zeolite and is selected from zeolites of the type MTW, FAU, BEA, MAZ, MOR, OFF, SAPO-5, or SAPO-11.

11. The process according to claim 10, wherein the zeolite is of the MTW, FAU or BEA type.

12. The process according to claim 1, wherein the zeolite is a medium-pore zeolite and is MCM-22 zeolite.

13. The process according to claim 1, wherein the water added is in an amount lower than or equal to 6% w/w with respect to the total mixture fed to the reactor.

14. The process according to claim 1, wherein the olefin is used in a mixture with the corresponding alcohol having the same number of carbon atoms as the olefin and which provides the same alkyl substituent by alkylation.

15. A process for the preparation of phenol, comprising the following steps:

(a) alkylating benzene with propylene to give cumene, carried out in accordance with claim 1, (b) oxidating the cumene thus obtained, (c) treating cumyl-hydroperoxide with acids in order to obtain a mixture of phenol and acetone, (d) hydrogenerating acetone to isopropanol, and (e) dehydrating isopropanol to propylene which is recycled to step (a).

16. The process according to claim 2, wherein:

in step (a) water is added to the mixture fed to the reactor; and in step (c) an aqueous phase is formed after cooling the reaction mixture, in addition to the organic phase.

17. The process according to claim 3, wherein:

in step (b) water is added to the mixture fed to the reactor; and in step (d) an aqueous phase is formed after cooling the reaction mixture, in addition to the organic phase.

* * * * *